US00PP28697P2

(12) United States Plant Patent
Farrow

(10) Patent No.: US PP28,697 P2
(45) Date of Patent: Nov. 28, 2017

(54) ***RHODODENDRON* 'MFARSS'**

(50) Latin Name: *Rhododendron hybrida*
Varietal Denomination: MFARSS

(71) Applicant: Michael Wayne Farrow, Warwick, MD (US)

(72) Inventor: Michael Wayne Farrow, Warwick, MD (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/330,250

(22) Filed: Aug. 29, 2016

(51) Int. Cl.
*A01H 5/00* (2006.01)

(52) U.S. Cl.
USPC ..... Plt./240

(58) Field of Classification Search
USPC ..... Plt./240
See application file for complete search history.

*Primary Examiner* — Annette Para
(74) *Attorney, Agent, or Firm* — Cassandra Bright

(57) ABSTRACT

A new and distinct *Rhododendron* cultivar named 'MFARSS' is disclosed, characterized by distinctive full double pink flowers. Plants are upright and vigorous. Plants bloom Spring, Summer and Fall and exhibit good tolerance to environmental stressors. The new cultivar is a *Rhododendron*, suitable for ornamental garden purposes.

2 Drawing Sheets

Figure 1:
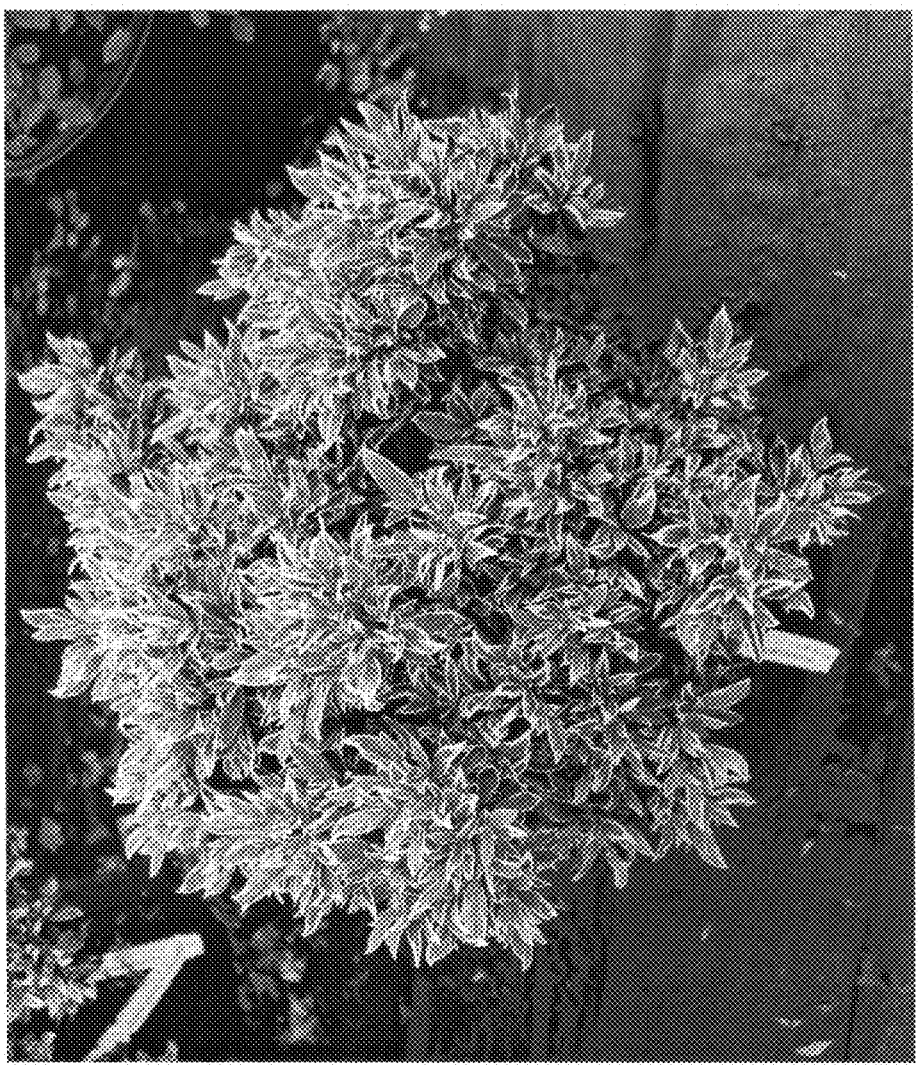

Latin name of the genus and species: *Rhododendron hybrida.*
Variety denomination: 'MFARSS'.

BACKGROUND OF THE INVENTION

The new cultivar is a product of chance discovery by the inventor, Michael Farrow. This new variety, hereinafter referred to as 'MFARSS', was discovered as a single branch, naturally occurring mutation of *Rhododendron* 'Farrow' U.S. Plant Pat. No. 22,209. The new variety was selected by the inventor during 2010 at a commercial nursery in Warwick, Md.

After identifying the new variety as a potentially interesting selection, the inventor first propagated the new variety by softwood cuttings at the same commercial nursery in Warwick, Md. The inventor continued controlled testing and propagation, assessing stability of the unique characteristics of this variety. At least three generations have been reproduced and have shown that the unique features of this cultivar are stable and reproduced true to type.

SUMMARY OF THE INVENTION

The cultivar 'MFARSS' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MFARSS' These characteristics in combination distinguish 'MFARSS' as a new and distinct *Rhododendron* cultivar:

1. Compact, densely growing plant habit.
2. Heavy blooming.
3. Distinct creamy variegated leaf margins.
4. Bright magenta pink flowers.

COMPARISON TO PARENT VARIETY

'MFARSS' is similar in most horticultural characteristics to the parent. Plants of the new cultivar 'MFARSS' however differ in the following:

1. The new variety has a denser, more compact plant habit.
2. The new variety produces more flowers per plant, and has small amount of re-blooming, after the initial heavy flush not found in the parent variety.

COMMERCIAL COMPARISON

'MFARSS' can be compared to the commercial variety *Rhododendron hybrida* 'Girard's Rose', unpatented. Plants of the new cultivar 'MFARSS' are similar to plants of 'Girard's Rose' in most horticultural characteristics, including a very similar flower color. However, plants of the new cultivar 'MFARSS' differ in the following:

1. Plants of the new variety are even more compact than plants of this comparator.
2. Plants of 'MFARSS' have variegated foliage, not found in this comparator variety.

'MFARSS' can be compared to the commercial variety *Rhododendron hybrida* 'Silver Sword', unpatented. Plants of the new cultivar 'MFARSS' are similar to plants of 'Silver Sword' in most horticultural characteristics, however, plants of the new cultivar 'MFARSS' differ in the following:

1. 'MFARSS' has a thicker cream colored leaf margin.
2. Plants of 'MFARSS' are more compact and dense than plants of 'Silver Sword'.
3. Foliage of 'MFARSS' has a more acute apex than foliage of 'Silver Sword'.
4. Plants of 'MFARSS' have a shorter mature height than plants of 'Silver Sword'.

BRIEF DESCRIPTION OF THE PHOTOGRAPHS

The accompanying photograph in FIG. 1 illustrates in full color a 2 year old plant of the new variety in a 5 gallon pot.

Figure 2:
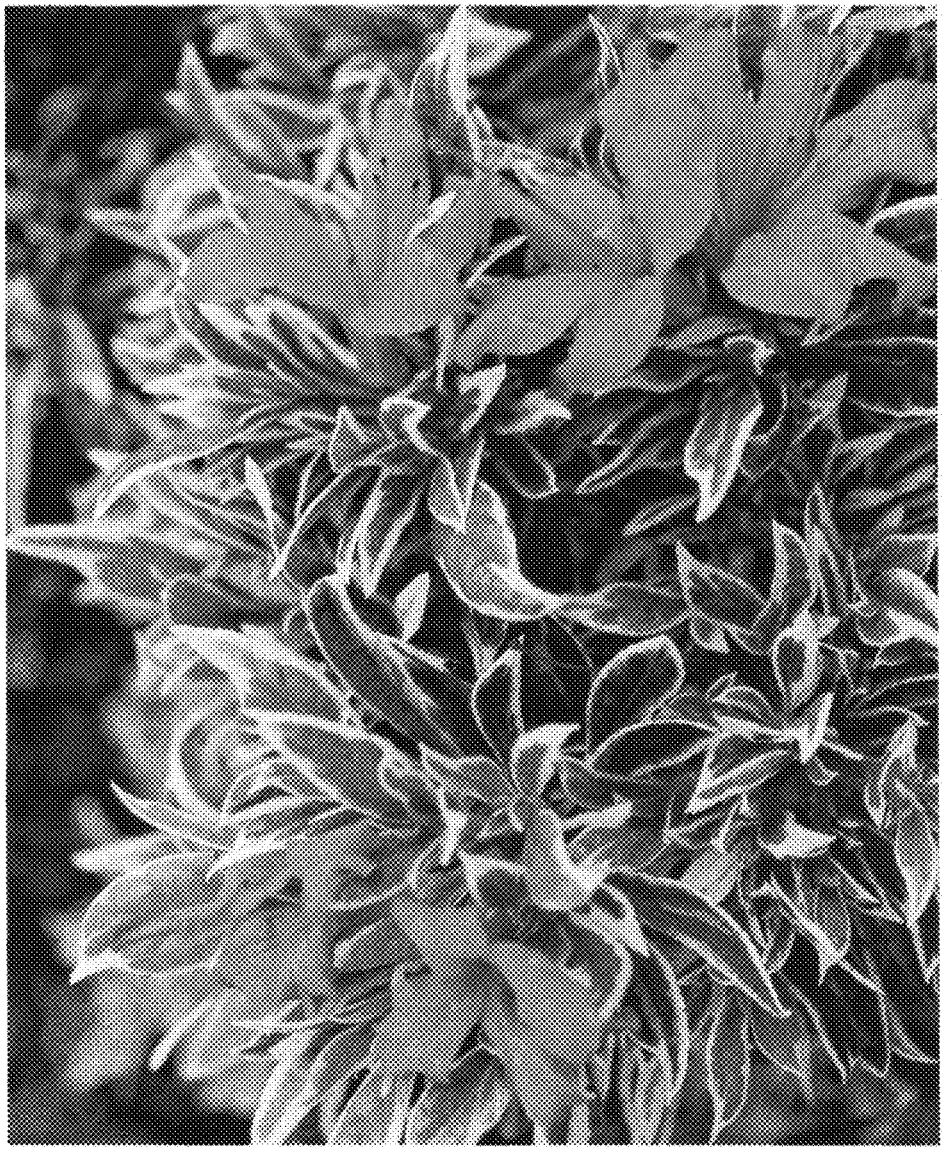

FIG. 2 illustrates in full color a close up of a typical flower and foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, fifth edition, except where general terms of ordinary dictionary significance are used. The following observations and measurements describe 'MFARSS' plants grown outdoors in Loxley, Ala. Plants are approximately 2 to 3 years old, in a 3 gallon nursery container. Measurements and numerical values represent averages of typical plant types.

Botanical classification: *Rhododendron hybrida* 'MFARSS'.

PROPAGATION

Typically by semi-hardwood cuttings in Spring and Summer.

Root description: Fine, fibrous young roots, well branched. Colored near RHS Grey-Brown 199A.

PLANT

Growth habit: Low, mounded evergreen shrub.

Height: Approximately 24 cm to top of foliar and flowering plane.

Plant spread: Approximately 33 cm.

Growth rate: Slow to moderate.

Branching characteristics: Very well branched with basal branches and lateral branches. Lateral branching encouraged by pinching.

Lateral branches:

Lateral branch quantity: Average 48.

Length of primary branches: Average range 19 to 25 cm.

Diameter of primary branches: Approximately 45 mm.

Primary branch strength: Strong.

Lateral branch color: Immature: Near Yellow-Green 144B. Mature: Near Greyed-Orange 165A.

Primary branch texture: Scaly, rough.

Lateral branch texture: Slightly pubescent.

Internode length: Average 1.3 cm.

Age of plant described: Approximately 2 to 3 years.

FOLIAGE

Leaf:

*Type*.—Simple.

*Arrangement*.—Alternate or whorled.

*Average length*.—Average 4.5 cm.

*Average width*.—Average 1.1 cm.

*Shape of blade*.—Lanceolate to oblanceolate.

*Apex*.—Acute.

*Base*.—Cuneate to attenuate.

*Attachment*.—Stalked.

*Margin*.—Entire. Undulate.

*Texture of top surface*.—Glabrous.

*Texture of bottom surface*.—Sparsely pubescent.

*Appearance*.—Upper surface glossy, under surface matte.

*Color*.—Young foliage upper side: Near Yellow-Green 146B, margins near Yellow 10D. Young foliage under side: Near Yellow-Green 146B, margins near Yellow 10D. Mature foliage upper side: Near Yellow-Green 146A, margins near Yellow 11D. Mature foliage under side: Near Yellow-Green 146B, margins near Yellow 11D.

*Venation*.—Type: Pinnate. Venation color upper side: Identical to leaf blade. Venation color under side: Identical to leaf blade.

*Petiole*.—Length: About 0.6 cm. Diameter: About 0.1 cm. Color: Upper Surface: Near RHS Yellow-Green 164C. Lower Surface: Near RHS Yellow-Green 146C. Texture: Upper and lower surfaces slightly pubescent.

FLOWER

Bloom period: Natural flowering begins in May, under conditions found in Michigan.

Flower:

*Arrangement*.—Axillary clusters of perfect, single funnel shaped individual flowers. Typically 2 to 5 flowers per cluster. About 160 flowers and buds on a plant in full bloom. Flower longevity approximately 3 weeks.

Flowers:

*Length*.—Average 4.0 cm.

*Diameter*.—Average 6.0 cm.

*Facing direction*.—Outwardly and upwardly facing.

*Persistent or self-cleaning*.—Self-cleaning.

*Fragrance*.—None.

Petals:

*Length*.—Approximately 2.5 cm.

*Width*.—Approximately 1.5 to 2.0 cm

*Apex*.—Acute, undulating and ruffled.

*Base*.—Fused.

*Shape of petal*.—Ovate.

*Petal margin*.—Entire, ruffled.

*Petal number*.—5.

*Petal texture*.—Smooth.

*Color*.—Upper surface at first opening: Near RHS Red-Purple N57A. Under surface at first opening: Near RHS Red-Purple N57A. Inner surface at maturity: Near RHS Red-Purple N57A. Outer surface at maturity: Near RHS Red-Purple N57A.

Bud:

*Shape*.—Elliptic.

*Length*.—2.4 cm.

*Diameter*.—1.2 cm.

*Color*.—Near RHS Red-Purple N57A.

Calyx/sepals: Star shaped calyx.

*Quantity per flower*.—5 sepals.

*Shape*.—Lanceolate.

*Length*.—9 mm.

*Width*.—3 mm.

*Apex*.—Narrowly acute.

*Base*.—Fused.

*Margin*.—Entire.

*Texture*.—All surfaces slightly pubescent.

*Color*.—Interior Surface: Near RHS Yellow-Green 145D. Outer Surface: Near RHS Yellow-Green 145D.

Peduncle: Not present, inflorescence pedicels emerge directly from node.

Pedicel:

*Length*.—Average 5 mm.

*Diameter*.—1 mm.

*Color*.—Near RHS Yellow-Green 145D, tinged near Red-Purple 57A.

*Texture*.—Slightly pubescent.

*Aspect*.—Straight. Angle of attachment, approximately 45° angle from stem.

*Strength*.—Strong.

REPRODUCTIVE ORGANS

Stamens:

*Number.*—5.

*Filament length.*—3 cm.

*Width.*—0.1 cm.

*Filament color.*—Near RHS Red-Purple 57A.

*Anthers.*—Shape: Spherical. Length: Less than 1 mm. Color: Near RHS Red-Purple 72A. Pollen: Scant, colored near Red-Purple 57A.

Pistil:

*Number.*—1.

*Length.*—Average 3.2 cm.

*Style.*—Length: Average 3.0. cm. Color: Near RHS Red-Purple N57C. Stigma: Globular, colored near Red-Purple N66A. Ovary: Colored near White 155C.

OTHER CHARACTERISTICS

Disease and pest resistance: Not observed to be susceptible nor resistant to normal diseases and pests of *Rhododendron.*

Temperature tolerance: Observed hardy to USDA Zone 7, potentially hardy to zone 6.

Fruit/seed production: Not observed to date.

What is claimed is:

1. A new and distinct cultivar of *Rhododendron* plant named 'MFARSS' as herein illustrated and described.

* * * * *